(12) United States Patent
Niebuhr et al.

(10) Patent No.: US 11,717,625 B2
(45) Date of Patent: Aug. 8, 2023

(54) COMPONENT PART AND BASE PART FOR AN INHALER, AND METHOD FOR MAKING SAME

(71) Applicant: KÖRBER TECHNOLOGIES GMBH, Hamburg (DE)

(72) Inventors: Gunnar Niebuhr, Hamburg (DE); Rene Schmidt, Buchholz (DE); Marc Kessler, Hamburg (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 411 days.

(21) Appl. No.: 16/648,482

(22) PCT Filed: Sep. 18, 2018

(86) PCT No.: PCT/EP2018/075165
§ 371 (c)(1),
(2) Date: Mar. 18, 2020

(87) PCT Pub. No.: WO2019/057694
PCT Pub. Date: Mar. 28, 2019

(65) Prior Publication Data
US 2020/0229499 A1    Jul. 23, 2020

(30) Foreign Application Priority Data
Sep. 19, 2017 (DE) ..................... 10 2017 121 664.2

(51) Int. Cl.
*A24F 13/00* (2006.01)
*A61M 15/08* (2006.01)
(Continued)

(52) U.S. Cl.
CPC ............ *A61M 15/08* (2013.01); *A24F 40/40* (2020.01); *A24F 40/50* (2020.01); *A24F 40/70* (2020.01);
(Continued)

(58) Field of Classification Search
CPC ....................................................... A24F 47/00
(Continued)

(56) References Cited

U.S. PATENT DOCUMENTS

| 8,998,632 B2 * | 4/2015 | Golko | H01R 13/6273 439/345 |
| 10,194,696 B2 * | 2/2019 | Matischek | A24F 40/65 |

(Continued)

FOREIGN PATENT DOCUMENTS

| CN | 103491815 | 1/2014 |
| CN | 104812260 | 7/2015 |

(Continued)

OTHER PUBLICATIONS

1st Examination Report issued by the German Patent and Trademark Office dated with respect to priority German Patent Application No. 10 2017 121 664.2.

(Continued)

*Primary Examiner* — Phuong K Dinh
(74) *Attorney, Agent, or Firm* — Saliwanchik, Lloyd & Eisenschenk

(57) ABSTRACT

The invention relates to a component part (1) for an inhaler (27), preferably for an electronic cigarette product, which component part comprises a carrier (2), an electric evaporator (3) arranged on the carrier (2) for evaporating liquid supplied to the evaporator (3), and an electric connection for supplying the evaporator (3) with electric energy and/or for receiving control signals for the evaporator (3). The electric connection comprises a plug connector part (7), which is configured for reversible interaction with a corresponding plug connector part (22) of the base part (20) of the inhaler (27). A base part (20) for an inhaler (27) comprises an electronic control device (21) and an electric connection for transmitting control signals to a component part (1) and/or (Continued)

for the electric supply of a component part (1) of the inhaler (27). The electric connection comprises a plug connector part (22), which is configured for reversible interaction with a corresponding plug connector part (7) of the component part (1).

24 Claims, 4 Drawing Sheets

(51) Int. Cl.

| | | |
|---|---|---|
| *A24F 40/70* | (2020.01) | |
| *A24F 40/40* | (2020.01) | |
| *A24F 40/50* | (2020.01) | |
| *H01R 24/62* | (2011.01) | |
| *H01R 105/00* | (2006.01) | |
| *H02J 7/00* | (2006.01) | |
| *A24F 40/10* | (2020.01) | |
| *A24F 40/65* | (2020.01) | |

(52) U.S. Cl.
CPC ............ *H01R 24/62* (2013.01); *A24F 40/10* (2020.01); *A24F 40/65* (2020.01); *H01R 2105/00* (2013.01); *H02J 7/0042* (2013.01)

(58) Field of Classification Search
USPC .................................................. 131/328–329
See application file for complete search history.

(56) References Cited

U.S. PATENT DOCUMENTS

| | | | |
|---|---|---|---|
| 10,757,975 B2 | 9/2020 | Batista et al. | |
| 2011/0226236 A1 | 9/2011 | Buchberger | |
| 2014/0060554 A1 | 3/2014 | Collett et al. | |
| 2014/0096781 A1* | 4/2014 | Sears ...................... | A24F 40/50 131/328 |
| 2014/0096782 A1 | 4/2014 | Ampolini et al. | |
| 2014/0261408 A1* | 9/2014 | DePiano ................. | H05B 3/04 128/202.21 |
| 2015/0181944 A1 | 7/2015 | Li et al. | |
| 2016/0262454 A1 | 9/2016 | Sears et al. | |
| 2016/0295913 A1 | 10/2016 | Guo et al. | |
| 2016/0302486 A1 | 10/2016 | Eroch | |
| 2016/0345626 A1* | 12/2016 | Wong ...................... | A24F 40/40 |
| 2017/0135402 A1 | 5/2017 | Zitzke | |
| 2017/0143042 A1 | 5/2017 | Batista et al. | |
| 2017/0215485 A1* | 8/2017 | Zitzke .................. | A61M 11/042 |
| 2017/0273358 A1 | 9/2017 | Batista et al. | |
| 2018/0140019 A1 | 5/2018 | Guo et al. | |
| 2018/0352863 A1 | 12/2018 | Nakano et al. | |
| 2021/0204602 A1 | 7/2021 | Buchberger | |

FOREIGN PATENT DOCUMENTS

| | | |
|---|---|---|
| CN | 205082675 U | 3/2016 |
| CN | 205082675 U | 3/2016 |
| CN | 106535680 | 3/2017 |
| CN | 206403199 U | 8/2017 |
| DE | 10 2014 207277 A1 | 10/2015 |
| DE | 10 2015 113193 A1 | 10/2016 |
| DE | 102015113193 | 10/2016 |
| DE | 102015115527 | 1/2017 |
| EP | 1154815 B1 | 7/2004 |
| EP | 3117860 | 1/2017 |
| EP | 3117860 A1 | 1/2017 |
| JP | 2017-522876 A | 8/2017 |
| KR | 10-2017-0020800 | 2/2017 |
| WO | 2012062247 | 5/2012 |
| WO | WO 2015/038981 A2 | 3/2015 |
| WO | WO 2016/005601 A1 | 1/2016 |
| WO | WO 2016/145072 A1 | 9/2016 |
| WO | WO 2017/141358 A1 | 8/2017 |

OTHER PUBLICATIONS

Examination Report issued by the Japanese Patent Office dated Oct. 25, 2022 with respect to the parallel Japanese patent application No. 2020-537048.
Notice of Korean Application Office Action, Application No. 10-2020-7009664, dated Apr. 20, 2023, 9 pages.
Search Report, Chinese Patent Application No. 201880060579.7, dated Feb. 23, 2023, 4 pages.

* cited by examiner

Fig. 2
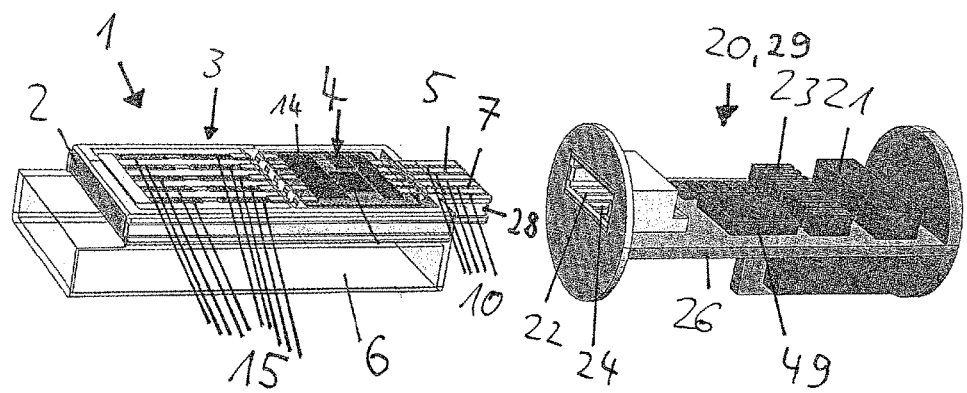
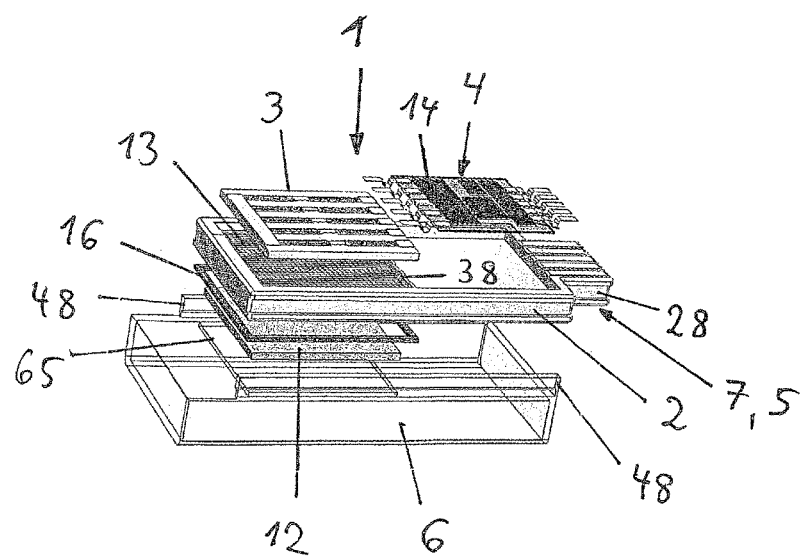
Fig. 3

COMPONENT PART AND BASE PART FOR AN INHALER, AND METHOD FOR MAKING SAME

CROSS REFERENCE TO RELATED APPLICATIONS

This application is a National Stage Application of International Application Number PCT/EP2018/075165, filed Sep. 18, 2018; which claims priority to German Patent Application No. 10 2017 121 664.2, filed Sep. 19, 2017.

FIELD OF INVENTION

The present invention relates to a component part for an inhaler, preferably for an electronic cigarette product, which component part comprises a carrier, an electric evaporator arranged on the carrier for evaporating liquid supplied to the evaporator, and an electric connection for supplying the evaporator with electric energy and/or for receiving control signals for the evaporator. The present invention further relates to a base part for an inhaler, which base part comprises an electronic control device and an electric connection for transmitting control signals to a component part and/or for the electric supply of a component part of the inhaler. The present invention further relates to a method for the production of such a component part and/or base part.

BACKGROUND OF THE INVENTION

A large proportion of the inhalers and electronic cigarette products on the market are based on the evaporation of a liquid containing flavouring substances and/or active ingredients. In principle, an energy store, a component part as a disposable part, a base part as a reusable part and a liquid storage tank are provided for this purpose.

A disposable cigarette product and embodiments of electronic cigarette products with reusable, replaceable, rechargeable or refillable components are described in US 2014/0060554 A1.

Reusable products are characterised by the fact that base components such as the housing, electronics and/or the energy store can be reused. The liquid storage tank and/or the evaporator can be exchangeable, for example.

An example of an electronic cigarette product having a reusable base unit with a battery and a replaceable or refillable cartridge is described in EP 1 154 815 B1.

A modular electronic cigarette product is described in DE 10 2014 207 277 A1. In this example, the electronic cigarette product is divided into a multiplicity of segments. Each segment comprises at least one component, for example an electric energy source, a liquid tank and a heating element.

Due to the variety of embodiments, different requirements are placed on the components of the electronic cigarette product in order to achieve a balance between quality, price and ease of assembly.

At present, there are no solutions where more than one heating channel can be controlled. A single-channel contacting system offers the possibility to control a single-channel heating device. Reference measurements between channels are not possible, and therefore no statements can be made about defective channels or dirty contacts.

The electric contacts are mainly arranged close to the evaporator and are therefore subject to contamination.

BRIEF SUMMARY OF THE INVENTION

The object of the present invention is to provide components for an inhaler that meet the requirements of different suppliers and can be integrated cost-effectively and by a simple assembly, as well as to specify corresponding production methods.

The object of the invention is achieved with the features of the independent claims.

The provision of plug connector parts to be connected to each other according to the invention allows a simple, fast and error-free connection of the component part with the base part. The invention provides an assembly-friendly and favourable, standardised electric interface or connection between the component part and the base part and allows system integration of a variety of evaporators and evaporator concepts. Due to the defined interface, tests desired during production can be carried out with little effort and in a standardised manner. Application of the invention in an automated assembly is possible.

Due to the integration of the evaporator into the component part, complicated cleaning of the evaporator is not necessary because the component part can be disposed of with the evaporator after its planned useful life.

Advantageously, the plug connector parts of the component part and of the base part are formed by a plug and a socket. Plug connectors are robust and allow a stable construction and thus maximum protection of the heating elements of the evaporator. It may be advantageous if the plug is arranged on the component part and the socket is arranged on the base part since, in this case, the component part is easier to slide into the base part. However, the reverse case is not excluded that the socket is arranged on the component part and the plug is arranged on the base part. A secure electric connection of the component part to the base part can be realised by a plug with particularly highly conductive contacts.

Preferably, the plug connector parts of the component part and of the base part each have at least three differently assignable or occupied metal contacts. This allows the control of a plurality of heating elements or heating channels as well as reference measurements between different heating elements or heating channels, in order to allow statements about defective heating channels or dirty contacts. Advantageously, at least four, further advantageously at least five differently assignable or occupied metal contacts are provided in order to allow a differentiated control and/or measurement of the evaporator with a corresponding number of lines. It is therefore advantageous if the electric connection comprises, in addition to the power supply lines, at least one digital data line and/or at least one analogue signal line between the component part and the base part.

In an advantageous embodiment, metal contacts are arranged in part at a top side and/or a bottom side of the plug connector part. This allows a compact design as well as a safe signal/energy transmission. In some embodiments, corresponding contacts on the top and on the bottom side of the plug connector part can be arranged rotationally symmetrically by 180° in each case (i.e. in a point mirrored manner) and be equally occupied. This has the advantage that when connecting the plug connector parts, it is not necessary to pay attention to their correct orientation to each other.

In an advantageous embodiment, the plug has a plate-shaped base part, wherein metal contacts are advantageously arranged at a top side and/or at a bottom side of the base part.

Preferably, the carrier of the component part has a defined liquid interface for the connection of the carrier with a liquid tank. This makes possible the simple and standardised connection of a variety of liquid tanks depending on the supplier. Preferably, the evaporator and the electronic components are arranged on one side of the plate-shaped carrier and the liquid interface on the other side of the plate-shaped carrier. In this case, the carrier advantageously has at least one through-opening for transporting liquid from the liquid interface to the evaporator. Advantageously, at least one capillary element can be arranged in the through-opening in order to support the liquid transport and liquid supply from the liquid interface to the evaporator.

Preferably, the component part has an electronic control device for controlling and/or regulating the evaporator. Preferably, the component part has an electronic memory for the permanent storage of an identifier for the component part. The base part advantageously comprises a data store in which control data for a plurality of identifiers corresponding to a plurality of different evaporators are permanently stored. As a result of connecting the component part to the base part, i.e. by connecting the corresponding plug connectors, the electronic control device of the base part can read out the identifier from the electronic memory of the component part and perform a type-specific individual control of the respective evaporator of the component part.

Preferably, the component part has one or more sensors for detecting operating states of the evaporator, for example a temperature sensor for measuring the heating temperature, also indirectly by measuring the heating resistors, and/or a pressure sensor for measuring the flow pressure. Advantageously, an electric connection between the electronic control device on the one hand and the evaporator and/or the sensors on the other hand, in addition to the power supply lines, has at least one analogue or digital signal transmission line, by means of which the sensor signals can be transmitted to the electronic control device.

Preferably, the base part has a defined battery interface for connecting the electronic control device to an energy storage unit. This makes possible the simple and standardised connection of a wide range of energy storage systems depending on the supplier. The battery interface has advantageously, in addition to the supply lines, at least one signal line or data line to allow the sending and receiving of signals or data between the energy storage unit and the electronic control device of the base part.

Advantageously, the base part has a wireless module for wireless communication with a user terminal. This allows the user to read data from the inhaler, make settings in the inhaler, and the like.

Preferably, the base part is a reusable part. In advantageous embodiments, the component part can be a disposable part. The component part can be a reusable part in other embodiments. It is conceivable, for example, to re-use the component part having the liquid tank and the evaporator after refilling.

BRIEF DESCRIPTION OF THE FIGURES

The invention is explained below on the basis of preferred embodiments with reference to the attached drawings, in which

FIG. 2 is a perspective view of an assembled component part and a control unit;

FIG. 3 is an exploded view of the component part from FIG. 2;

DETAILED DESCRIPTION

Figure 1:
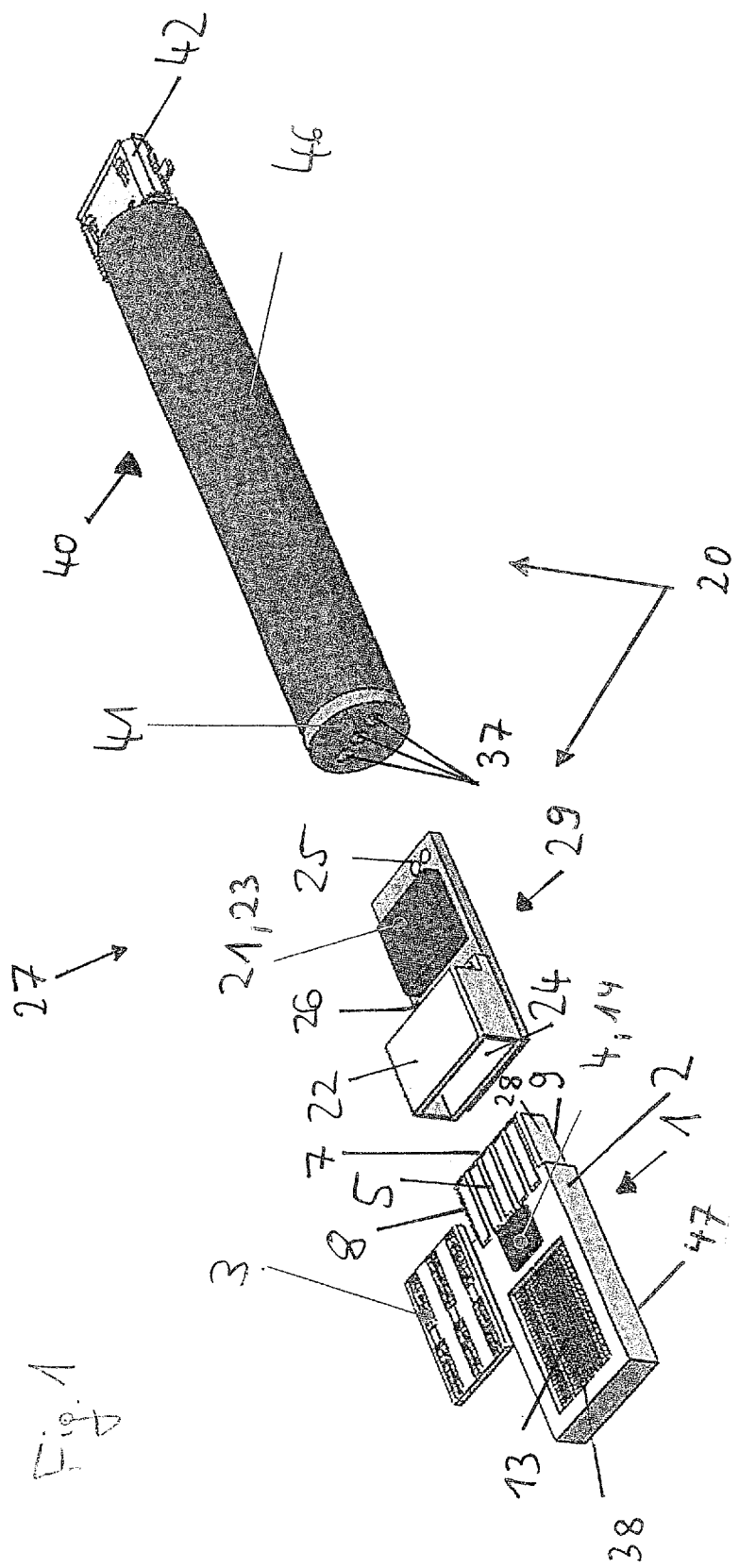
FIG. 1 shows components of an inhaler having a component part and a base part in an embodiment of the invention.

The rod-shaped inhaler 27 shown in FIG. 1 comprises a component part 1, which can be a disposable part or a reusable part, and a reusable base part 20, which is thus advantageously a reusable part.

The component part 1 comprises a carrier 2, which can also be called a carrier plate, and a liquid tank 6 to be connected or that is connected to the carrier 2. On the carrier 2, a digital electronic control device 4 is arranged, for example an application-specific integrated circuit (ASIC). Preferably, the electronic control device 4 comprises electronic components to make measurements on reference resistors (shunts), and other integrated control electronics, such as MOSFETs for circuitry, reference resistors (shunts) for resistance measurement, and sensors 51. The electronic control device 4 preferably comprises a multiplexer and/or a sliding register to carry out the control of various channels of the evaporator 3. In general, the carrier 2 serves to receive all the electronic components used for controlling the evaporator 3 and the heating elements 15, in particular the control device 4, MOSFETs, shunts etc., as well the electronic identification hardware, in particular the electronic memory 14.

The carrier 2 also has an electric plug connector part 7 in the form of an electric plug 5 having a plurality of electric contacts 10. The contacts 10 are connected to the electronic components 4, 14 by means of electric wires, which run at least in part on and/or the carrier 2, in order to transmit sensor signals, control signals and/or electric energy. The carrier 2 that is advantageously continuous and shape-stable may consist of a suitable, advantageously non-conductive material, for example ceramic or a suitable plastics material, in particular PEEK, or fibre-reinforced plastics material. Sensors, such as temperature sensors for measuring the heating temperature and/or a pressure sensor for measuring the flow pressure, can be provided on the component part.

On the carrier 2, an evaporator 3 is arranged, which evaporates the liquid supplied from the liquid tank 6. The carrier 2 thus accommodates the evaporator 3 including the contacting thereof. The evaporator 3 that is in particular electric has at least one, preferably a plurality of electric resistance heating elements 15. The evaporator 3 is preferably arranged at a top side of the carrier 2. Each of the heating elements 15 can be controlled by the electronic control device 4 and can be heated by electricity from the energy store 46 to evaporate adjacent liquid on the heating elements 15.

Each heating element 15 is preferably separately controllable or heatable. This is preferably accomplished by means of a multi-channel contacting of the evaporator 3, in FIGS. 2 and 4 by means of five-channel contacting, for example. This also allows reference measurements between different channels, which allows statements about defective channels or dirty contacts. The control of various heating channels can be advantageously carried out by a multiplexer and/or a sliding register. For example, each of the heating elements 15 can be heated with a different temperature, cycle duration, power, frequency and/or a different duty cycle in order to achieve optimal administration of flavours and/or active ingredients, of which an active ingredient may be nicotine, for example.

The base part 20 comprises a control unit 29 and an energy storage unit 40 to be connected to the control unit 29.

The control unit comprises an electronic control device 21 and an electric socket 22 electrically connected to the electronic control device 21. The electronic control device 21 and the electric socket 22 are advantageously arranged on a common circuit board 26. The base part 20 can have a programming interface 25 with, for example, two contacts, by means of which the control device 21 is programmable, for example, during production of the control unit 29.

The electric plug 5 and the electric socket 22 are set up accordingly, such that by inserting the plug 5 into the socket 22, an electric connection is established between the component part 1 and the base part 20 for the transmission of signals, data and/or electric power. In particular, the electric connection, which can be produced by the plug 5 and the socket 22, serves to supply the electric and electronic components of the component part 1 from the energy store 40, and to transmit signals between the component part 1 and the base part 20. In the component part 1, the supply currents and signals from the plug 5 are forwarded to the evaporator 3 and/or to sensors. Advantageously, the plug 5 and the socket 22 each have the same number of electric contacts 10.

Preferably, the plug 5 has a plate-shaped base part 28 having a top side 8 and a bottom side 9, wherein on the top side 8 and/or on the bottom side 9 strip-shaped, electric metal contacts 10 are provided. The base part 28 consists of a suitable material and can be formed, for example, in one piece or integrally with the carrier 2, as can be seen best in FIG. 3. Preferably, the plug 5 has electric contacts 10 on both sides, i.e. both on the top side 8 and on the bottom side 9. The contacts on the top side 8 and on the bottom side 9 of the plug 5 can be assigned differently, such that a multiplicity of electric contacts 10 can be provided in a small space. In other advantageous embodiments, the contacts 10 on the top side 8 and a corresponding number of contacts on the bottom side 9 are arranged rotationally symmetrically by 180° and are equally occupied. This has the advantage that when connecting the plug connector parts 7, 22, it is not necessary to take into account the correct orientation; instead, the plug 5 can be inserted into the socket 22 in both orientations and in both cases the intended electric connection is established.

In a preferred embodiment, the plug 5 has five differently occupied contacts 10.

In order to connect the component part 1 to the base part 20, the component part 1 is inserted into the base part 20 parallel to the longitudinal axis thereof, whereby the plug 5 is inserted into the socket 22 and the electric connection is established.

The electronic control device 4 of the component part 1 preferably comprises an electronic memory 14. In the electronic memory 14, an identifier or ID (identification information) of the component part 1 is advantageously permanently stored. As a result of connecting a component part 1 to a base part 20, as a result of inserting the plug 5 into the socket 22, the electronic control device 21 can read out the identifier from the memory 14 and realise a type-specific individual control of the respective evaporator 3 on the component part 1. In the electronic memory 14, it is also possible to store control, regulating and/or measurement parameters, which can be transferred to the base part and by means of which the base part 20 controls or heats up the evaporator 3.

The electronic control device 4 and the control of the evaporators 3 are preferably specifically programmed for each liquid located in the liquid storage tank 6 in order to achieve an optimal flavour and/or active ingredient administration. The placement of the control device 4 in the component part 1 facilitates the design of electronic components and electric connection devices.

The electronic control device 21 of the base part 20 advantageously comprises a data store 23. In the data store, control data for a plurality of identifiers are preferably stored according to a plurality of different evaporators or evaporator types, for example in the form of a database. If the electronic control device 21 reads an identifier from the memory 14 of the component part 1, it can retrieve the control data assigned to this identifier from the data store 23 and perform the control of the evaporator 3 according to the type. According to this, items of information about the evaporator 3, evaporator type, residual quantity of the liquids present in the liquid storage tank 6, the liquid composition and/or the characteristics of the evaporator 3 are advantageously attributed to the ID of a component part 1 in the data store 23.

The energy storage unit 40 comprises an energy store 46, a battery interface 41 for connecting the control unit 29 to the energy storage unit 40, and a charging interface 42. The control unit 29 is supplied with power via the battery interface 41. Furthermore, signals can be transmitted between the energy storage unit 40 and the control unit 29 via the battery interface 41. Therefore, the battery interface 41 advantageously comprises at least three electric contacts 37, namely two electric contacts 37 for the power supply lines 36 (see FIG. 6) and at least one electric contact 37 for at least one analogue or digital signal transmission line 31.

In an advantageous embodiment, the at least one signal transmission line 31 comprises a digital data bus, for example, a single-wire (1-wire) bus. In other embodiments, a multi-wire bus 31 may be provided. For example, information about the state of charge of the energy store or diagnostic data can be provided by means of the electric connection between the base part 20 and the energy storage unit 40. For example, information about the state of charge of the energy store 46 or diagnostic data can be transferred between the control unit 29 and the energy storage unit 40 by means of the signal transmission line 31.

The energy store 46 can be a disposable battery or a rechargeable battery, such as a lithium-ion battery. In the example shown, the energy store 46 is a rechargeable battery, which can be charged via the charging interface 42, for example a USB interface. In the energy storage unit 40, an electronic control device 43 is preferably integrated, which can comprise safety electronics 44 and/or charging electronics 45. The safety electronics 44 serve to monitor the function of the energy store 46 and, for example, to prevent overheating. The charging electronics 45 control the charging of the energy store 46 via the charging interface 42. To charge the energy store 46, the user can connect the charging interface 42 to a power source, for example the power grid. The charging interface 42 can also be used for signal transmission, for example for the exchange of data between a mobile terminal of the user, for example, and the electronic control device 21, in order to adjust, program and/or collect and/or enter data, such as user data and/or measured values.

The energy storage unit 46 and the energy store 40 including charging electronics 45 are advantageously designed to be supplier-specific. The battery interface 41 between the energy storage unit 46 and control unit 29 can therefore advantageously have a supplier-specific design.

In the mounted state, the base part 20 is rod-shaped and/or cylindrical overall and thus has two end faces. The plug connector 22 of the base part 20 is advantageously arranged at one of the end faces of the base part 20, as is apparent from FIG. 1. This facilitates the insertion of the component part 1 into the base part 20 and thus the handling of the inhaler. The charging interface 42 is advantageously arranged at the end face of the base part 20 that is opposite the plug connector 22, as is also apparent from FIG. 1. This facilitates insertion of an external charging plug into the charging interface 42 and thus also the handling of the inhaler.

The component part 1 has a liquid interface 47 for the connection of the liquid tank 6 to the carrier 2. Due to the standardised liquid interface 47, a multiplicity of different liquid tanks 6 can be used, i.e. the liquid tank 6 can be of a supplier-specific design. The liquid interface 47 is advantageously arranged on the bottom side, or at the (top) side of the carrier that is opposite the evaporator 3, where the liquid is supplied from the reservoir 6. The liquid storage tank 6 may be, for example, movable along a guide 48 on the carrier 2; other connections are possible. The connection can be reversible to allow the user to replace the liquid storage tank 6. The liquid storage tank 6 can be refillable, wherein the component part 1 in this case is a reusable part.

Figure 5:
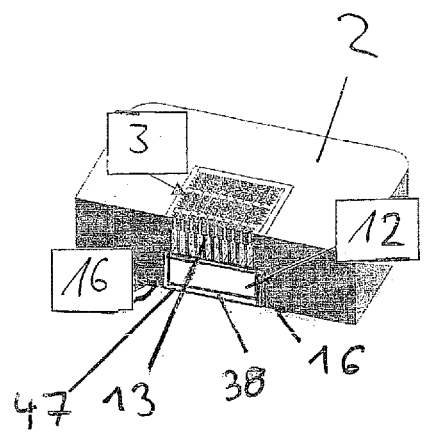
FIG. 5 is a cross section through the component part shown in FIG. 4 in the region of the evaporator.

The carrier 2 has one or more through-openings 38 to transport liquid from an opening 65 of the liquid tank 6 to the evaporator 3 and evaporate there. This can be seen in the cross section according to FIG. 5. Between the evaporator 3 and the liquid storage tank 6, a capillary element 12 is advantageously provided, which may be inserted for example in the opening 65 and supports the capillary liquid conveying from the liquid tank 6 to the evaporator 3. The capillary element 12, may be, for example, an open-pored foamed element or a sponge element.

Between the evaporator 3 and the liquid storage tank 6, a capillary element 13 may further be provided, which conveys liquid by means of capillary action, for example by means of microchannels, from the liquid storage tank 6 to the evaporator 3. The capillary element 13 can be a lamellar structure. On the side of carrier 2 opposite the liquid interface 47, the evaporated liquid is discharged via an air flow in order to be inhaled by the consumer.

The joint between the carrier 2 and the liquid tank may be advantageously sealed by a seal 16 surrounding the opening 65 or through-opening 38.

Figure 4:
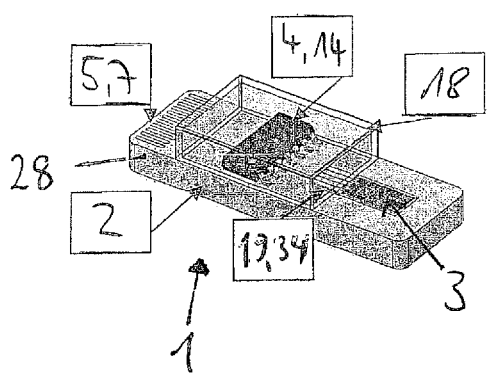
FIG. 4 is a perspective view of a component part in a further embodiment.

In the embodiment shown in FIG. 4, the component part 1 has a protective inlay 18. The protective inlay 18 hermetically encloses the electronic components 4, 14 for their protection, in particular the electronic control device 4, the electronic memory 14 and optionally the contact conductor 19 between the evaporator 3 and the electronic control device 4. The protective inlay 18 can be produced, for example, by casting an insulating mass. By enclosing or encapsulating the electronics, various electronic components can be integrated into the component part 1 independently of the material, for example MOSFETs, RFIDs, shunt resistors, level sensor, other sensors, etc. By encapsulating, unwanted substances can also be hermetically enclosed. Separation of the liquid part from the resistance heating elements 15 is possible.

In the encapsulated plug 5, the plug contacts 10 of the plug 5 are advantageously separated from the fluidic part, in order to reduce or prevent contamination of the contacts 10 and the contact conductors 19, 34. The structure with the carrier 2 is particularly stable and thus offers maximum protection of the heating element 3 or the heater structures.

The guidance of the contacts 19, 34 shown in FIG. 4 at least in part on and/or in the carrier 2 leads to low transition resistors and allows a control with low voltages, since the electric contacts on or in the carrier 2 are not separated or separable. The removal and encapsulation of the electronics and the direct or protected connection to the evaporator 3 are advantageous for the regulation and/or control, inter alia because the connecting paths are short. Due to the short distances between the evaporator 3 and the control device 4, a control of the evaporator 3 in the frequency range between 1 Hz to 20 kHz is possible.

By connecting the evaporator to the component part 1, a flexible integration of different evaporators 3 and heater structures or heating elements 15 is possible. The design of the component part 1 with the continuous carrier 2 is optimised for an evaporator 3 designed as a microelectromechanical system (MEMS). Here, for example, evaporators 3 with conduction or micro-channels are possible, as described in DE 10 2016 120 803.5, the disclosure content of which is included in the present application in this regard. Bionic heating structures, such as bionic nets, are also possible for the evaporator 3. Evaporators 3 with heating structures as described in DE 10 2017 111 119.0 are also possible, the disclosure content of which is included in the present application in this regard.

The heating element 15 can be controlled or heated by the electronic control device 4 with the desired frequency. For example, identification information is stored in the electric memory 14, for which a heating scheme or a parameter set corresponding to the respectively used evaporator 3 for regulating and/or controlling the evaporator 3 is stored in the electronic control device 21 or the data store 23 of the base part 20. The transmission of control parameters from the component part 1 to the base part 20 in addition to or instead of the identification information is also conceivable.

Figure 6:
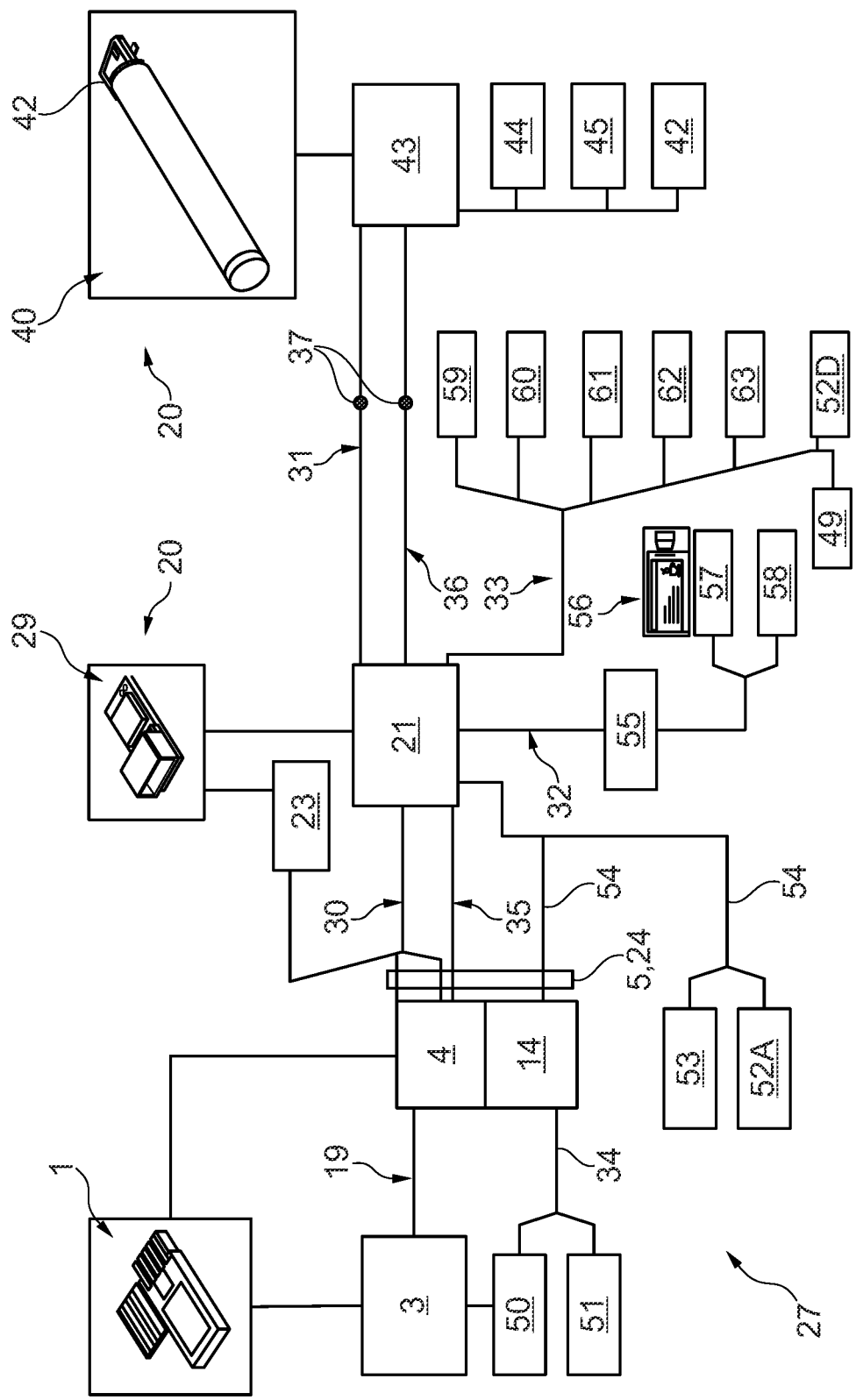
FIG. 6 is a schematic electronic plugging diagram of the inhaler.

In the following, an advantageous electric interconnection of the inhaler 27 is explained on the basis of FIG. 6. The component part 1 comprises the evaporator 3, which is designed, for example, as a silicon (Si) heater, having an electronic control device 4 with the electronic memory 14. The heating resistors 50 of the heating elements 15 can be measured by the control device 4, from which, for example, the evaporation temperature can be determined. Preferably, one or more sensors 51 can be provided for measuring an operating state, for example, the fill level of the liquid tank 6 or the heating temperature. The fill level of the liquid tank 6 can be measured capacitively, for example. In addition, the component part 1 can, for example, have a sensor for measuring the air pressure in the air flow.

The transmission of the measurement data from the heating resistor(s) 50 and/or from the sensors 51 to the control device 4 is preferably analogue. According to this, between the evaporator 3 or the sensors 50, 51 and the control device 4, advantageously at least one analogue signal line 34 is provided, in addition to the supply lines 19 for supplying power to the evaporator 3.

The component part 1 is supplied from the base part 20 via power supply lines 35.

The component part 1 is advantageously connected to the base part 20 via at least a 1-wire digital data bus 30. The data bus 30 is preferably a serial data bus, for example an inter-integrated circuit bus (I2C bus). The electronic control device 21 preferably comprises a microcontroller or microprocessor, and/or a wireless module 49, preferably a Bluetooth and/or a WLAN module to communicate with a user's mobile device.

In addition, one or a plurality of analogue measuring or signal lines 54 can be provided between the component part 1 and the base part 20. In the embodiment of FIGS. 1 to 3, for example, two supply lines 35, two digital data lines for the data bus 30 and one analogue signal line 54 are provided, according to which a total of five lines and five correspondingly occupied contacts 10 are provided. A different number of lines 30, 35, 54 is of course possible.

Optionally, one or more extensions 55 can be connected to the electronic control device 21, for example via a digital data bus, such as a serial peripheral interface bus (SPI bus). For example, the extensions 55 may comprise a display 56, such as an electronic paper display (E-Paper) 57 and/or an OLED display 58. Other extensions 55 for the output of information, such as status lights or acoustic output devices, are also conceivable.

The base part 20 can have one or more analogue sensors 52A, in particular a vapour quantity or Fumex sensor, and/or one or more analogue control devices 53, in particular a vapour quantity control. The analogue sensors 52A and/or the analogue control devices 53 are expediently connected by one or more analogue signal lines 54 to the control device 21.

Via an input/output (I/O) interface 33, function and/or operating devices of the base part 20 can be connected to the electronic control device 21, for example optionally a vapour quantity sensor 52 (Fumex measurement), optionally a wireless locator device 59 for finding nearby electronic cigarette products (Zig-Finder), one or a plurality of sensors 61 and/or one or a plurality of switches 62, in particular for the operation of the base part 20 by the consumers, optionally a converter 63, especially a DC voltage converter, such as an upward converter (step-up-converter), to convert the DC voltage provided by the DC voltage source 46 to the desired heating voltage for the resistance heating elements 15, and/or the wireless module 49 for communication with a user terminal.

The I/O interface 33 can also have one or more programmable channels (pins) 60.

The digital data store 23 of the base part 20 can optionally have a memory expansion, for example, by means of an external memory card that can be used in the inhaler 27. Control parameters, control software and/or user data are stored or can be stored in the data store 23. The data store 23 is connected, for example, via the data bus 30 to the electronic control device 21. The data store 23 can be addressed via the programming interface 25, the charging interface 42 and/or via the wireless module 49.

The construction of the inhaler 27 having a component part 1 and a separate base part 20 offers high ease of assembly and can be used in automated assembly. Cleanroom production is possible to allow the evaporator 3 and/or encapsulated electronic components of the highest quality to be produced. The high standardisation of the connection devices and the individualisation possibilities of the electronics allows the implementation of all evaporators on the market.

The electric plug 5, the electric socket 22, the electric battery interface 41, the charging interface 42, the liquid interface 47 and/or the interface of the evaporator 3 to the air flow provide clearly defined, standardised interfaces. In particular, the component part 1 has clearly defined and standardised interfaces with the base part 20, with the liquid reservoir 6, and with the air flow.

EMBODIMENTS

Embodiment 1. Component part (1) for an inhaler (27), preferably for an electronic cigarette product, comprising
   a carrier (2),
   an electric evaporator (3) arranged on the carrier (2) for evaporating the liquid supplied to the evaporator (3), and
   an electric connection for supplying the evaporator (3) with electric energy and/or for receiving control signals for the evaporator (3), characterised in that the electric connection comprises a plug connector part (7) which is arranged for reversible interaction with a corresponding plug connector part (22) of a base part (20) of the inhaler (27).

Embodiment 2. Component part according to any of the preceding embodiments, characterised in that the carrier (2) has a liquid interface (47) for standardised connection with a liquid tank (6).

Embodiment 3. Component part according to embodiment 2, characterised in that the carrier (2) has at least one through-opening (38) for the transport of liquid from the liquid interface (47) to the evaporator (3).

Embodiment 4. Component part according to embodiment 3, characterised in that a capillary element (12) is arranged in the through-opening (38).

Embodiment 5. Component part according to any of the preceding embodiments, characterised in that the component part (1) has an electronic control device (4) for controlling and/or regulating the evaporator (3).

Embodiment 6. Component part according to embodiment 5, characterised in that an electric connection between the electronic control device (4) and the evaporator (3) and/or sensors (50, 51) has power supply lines (19) and at least one signal transmission line (34).

Embodiment 7. Component part according to any of the preceding embodiments, characterised in that the component part (1) has an electronic memory (14) for the permanent storage of an identifier for the component part (1).

Embodiment 8. Base part (20) for an inhaler (27), comprising
   an electronic control device (21), and
   an electric connection for sending control signals to a component part (1) and/or for the electric supply of a component part (1) of the inhaler (27), characterised in that
   the electric connection comprises a plug connector part (22) which is arranged for reversible interaction with a corresponding plug connector part (7) of the component part (1).

Embodiment 9. Base part according to embodiment 8, characterised in that the base part (20) has a battery interface (41) for connecting the electronic control device (21) to an energy storage unit (40).

Embodiment 10. Base part according to embodiment 9, characterised in that the battery interface (41) has supply lines (36) and at least one signal line or data line (31).

Embodiment 11. Base part according to any of embodiments 8 to 10, characterised in that the base part (20) has a wireless module (49) for wireless communication with a user terminal.

Embodiment 12. Base part according to any of embodiments 8 to 11, characterised in that the base part (20) comprises a data store (23) in which control data for a plurality of identifiers corresponding to a plurality of different evaporators (3) are permanently stored.

Embodiment 13. Component part or base part according to any of the preceding embodiments, characterised in that the plug connector parts (7; 22) each have at least three metal contacts (10) that can be occupied differently.

Embodiment 14. Component part or base part according to any of the preceding embodiments, characterised in that, in the case of electric connection between the component part (1) and the base part (20), this connection comprises energy supply lines (35) and at least one digital data line (30) and/or at least one analogue signal line (54).

Embodiment 15. Component part or base part according to any of the preceding embodiments, characterised in that the plug connector parts (7; 22) comprise a plug (5) and a corresponding socket (24).

Embodiment 16. Component part or base part according to embodiment 15, characterised in that the plug (5) has a plate-shaped base part (28).

Embodiment 17. Component part or base part according to either embodiment 15 or embodiment 16, characterised in that metal contacts (10) are provided on a top side (8) and/or on a bottom side (9) of the plug (7).

Embodiment 18. Inhaler comprising at least one component part (1) and at least one base part (20) according to one or more of the preceding embodiments.

Embodiment 19. Method for the production of a component part (1) and/or a base part (20), preferably according to one or more of embodiments 1 to 17, in particular for an inhaler or in the course of production of an inhaler (27) preferably according to embodiment 18, characterised in that the component part (1) and/or the base part (20) is produced as a module, which is supplied or can be supplied to a production stream for an inhaler (27).

Embodiment 20. Method for the production, in particular according to embodiment 19, of a component part (1) and/or a base part (20) according to one or more of embodiments 1 to 17, characterised in that an evaporator (3), preferably a MEMS evaporator, is mounted on a carrier (2) having an electric connection for supplying the evaporator (3) with electric energy and/or for receiving control signals for the evaporator (3), wherein the electric connection comprises a connector part (7).

Embodiment 21. Method according to embodiment 20, characterised in that the carrier (2) is provided with a liquid interface (47) for the standardised connection with a liquid tank (6).

Embodiment 22. Method for the production, in particular according to any of embodiments 19 to 21, of a component part (1) and/or a base part (20) according to one or more of embodiments 1 to 17, characterised in that an electronic control device (21) for the electric connection and/or for sending control signals to a component part (1) and/or for the electric supply of a component part (1) is equipped with a plug connector part (22) which is used for reversible interaction with a corresponding plug connector part (7) of the component part (1).

Embodiment 23. Method for the production, in particular according to any of embodiments 19 to 22, of a component part (1) and/or a base part (20) according to one or more of the embodiments 1 to 17, characterised in that the plug connector parts (7; 22) are each provided with at least three differently occupiable metal contacts (10) that are preferably highly conductive.

Embodiment 24. Method for the production, in particular according to any of embodiments 19 to 23, of a component part (1) and/or a base part (20) according to one or more of embodiments 1 to 17, characterised in that a protective inlay (18) is provided which hermetically encloses the electronic components (4, 14) and which is produced, in particular, by casting an insulating mass.

The invention claimed is:

1. A component part for an inhaler, the component part comprising:
a carrier;
an electric evaporator disposed on the carrier for evaporating liquid supplied to the electric evaporator supplied from a liquid tank in operable communication with the electric evaporator;
one or more sensors disposed on the carrier for measuring an operation state of the component part;
an electric connection disposed on the carrier for supplying the electric evaporator with electric energy and/or for receiving control signals for the electric evaporator, wherein the electric connection comprises a plug connector part that is arranged for reversible interaction with a corresponding plug connector part of a base part of the inhaler; and
an electronic control device dispose on the carrier for controlling and/or regulating the electric evaporator, wherein the electric evaporator comprises at least one electric resistance heating element,
wherein the at least one resistance heating element comprises heating resistors that are measured by the electronic control device,
wherein transmission of measurement data from the heating resistors and/or from the one or more sensors to the electric control device is analog, and
wherein the plug connector part of the electric connection comprises electric contacts for power supply lines, a digital data bus comprising at least one wire, and at least one analog signal line.

2. The component part according to claim 1, wherein the carrier has a liquid interface for standardised connection with the liquid tank.

3. The component part according to claim 2, wherein the carrier has at least one through-opening for transport of a liquid from the liquid interface to the electric evaporator.

4. The component part according to claim 3, wherein a capillary element is arranged in the at least one through-opening.

5. The component part according to claim 1, wherein an electric connection between the electronic control device and the electric evaporator and/or the one or more sensors has the power supply lines and the at least one analog signal line.

6. The component part according to claim 1, wherein the electric contacts of the plug connector part of the electric connection comprises at least three metal contacts that can be occupied differently.

7. The component part according to claim 1, wherein when the electric connection between the component part and the base part is made, this electric connection is accomplished via the power supply lines and the at least one analog signal line.

8. The component part according to claim 1, wherein the plug connector part comprises a plug and a corresponding socket.

9. The component part according to claim 8, wherein the plug has a plate-shaped base part.

10. The component part according to claim 8, wherein the electric contacts of the plug connector part of the electric connection comprise metal contacts provided on a top side and/or on a bottom side of the plug.

11. A component part for an inhaler, the component part comprising:
a carrier;
an electric evaporator disposed on the carrier for evaporating liquid supplied to the electric evaporator supplied from a liquid tank in operable communication with the electric evaporator;

one or more sensors disposed on the carrier for measuring an operation state of the component part; and an electric connection disposed on the carrier for supplying the electric evaporator with electric energy and/or for receiving control signals for the electric evaporator, wherein the electric connection comprises a plug connector part that is arranged for reversible interaction with a corresponding plug connector part of a base part of the inhaler, wherein the component part has an electronic memory disposed on the carrier for the permanent storage of an identifier for the component part, wherein the electric evaporator comprises at least one electric resistance heating element, wherein the at least one resistance heating element comprises heating resistors that are measured by an electronic control device, wherein transmission of measurement data from the heating resistors and/or from the one or more sensors to the electronic control device is analog, and wherein the plug connector part of the electric connection comprises electric contracts for power supply lines, a digital data bus comprising at least one wire, and at least one analog signal line.

12. The component part according to claim 11, wherein the carrier has a liquid interface for standardised connection with the liquid tank.

13. The component part according to claim 12, wherein the carrier has at least one through-opening for transport of a liquid from the liquid interface to the electric evaporator.

14. The component part according to claim 11, wherein the electric contacts of the plug connector part of the electric connection comprises at least three metal contacts that can be occupied differently.

15. The component part according to claim 11, wherein when the electric connection between the component part and the base part is made, this electric connection is accomplished via the power supply lines and the at least one analog signal line.

16. The component part according to claim 11, wherein the plug connector part comprises a plug and a corresponding socket.

17. The component part according to claim 16, wherein the plug has a plate-shaped base part.

18. The component part according to claim 16, wherein the electric contacts of the plug connector part of the electric connection comprise metal contacts provided on a top side and/or on a bottom side of the plug.

19. An inhaler, comprising:
a component part for the inhaler,
wherein the component part comprises:
a carrier;
an electric evaporator disposed on the carrier for evaporating liquid supplied to the electric evaporator supplied from a liquid tank in operable communication with the electric evaporator;

an electric connection disposed on the carrier for supplying the electric evaporator with electric energy and/or for receiving control signals for the electric evaporator, wherein the electric connection comprises a plug connector part that is arranged for reversible interaction with a corresponding plug connector part of a base part;

one or more sensors disposed on the carrier for measuring an operation state of the component part; and an electronic control device disposed on the carrier for controlling and/or regulating the electric evaporator, wherein the electric evaporator comprises at least one electric resistance heating element, wherein the at least one resistance heating element comprises heating resistors that are measured by the electronic control device, wherein transmission of measurement data from the heating resistors and/or from the one or more sensors to the electronic control device is analog, and wherein the plug connector part of the electric connection comprises electric contacts for power supply lines, a digital data bus comprising at least one wire, and at least one analog signal line.

20. The inhaler according to claim 19, wherein the base part comprises:
a second electric connection for sending control signals to the component part and/or for the electric supply of the component part, and
wherein the second electric connection comprises the corresponding plug connector part which is arranged for reversible interaction with the plug connector part of the component part.

21. The inhaler according to claim 20, further comprising:
a battery interface for connecting the second electronic control device to an energy storage unit.

22. The inhaler according to claim 21, wherein the battery interface has the power supply lines and the at least one analog signal line.

23. The inhaler according to claim 20, further comprising:
a wireless module for wireless communication with a user terminal.

24. The inhaler according to claim 20, further comprising:
a data store in which control data for a plurality of identifiers corresponding to a plurality of different evaporators are permanently stored.

* * * * *